(12) United States Patent
Hatch et al.

(10) Patent No.: US 10,751,483 B2
(45) Date of Patent: Aug. 25, 2020

(54) MEDICAMENT DELIVERY DEVICE HAVING GAS PROPELLANT

(71) Applicant: Consort Medical PLC, Hemel Hempstead (GB)

(72) Inventors: Steven Hatch, Cambridgeshire (GB); Alastair Willoughby, Cambridgeshire (GB); Guy Moseley, Cambridgeshire (GB); Dan Garson, Cambridgeshire (GB)

(73) Assignee: Consort Medical PLC, Hemel Hempstead (GB)

( * ) Notice: Subject to any disclaimer, the term of this patent is extended or adjusted under 35 U.S.C. 154(b) by 313 days.

(21) Appl. No.: 15/567,901

(22) PCT Filed: Apr. 21, 2016

(86) PCT No.: PCT/GB2016/051114
§ 371 (c)(1),
(2) Date: Oct. 19, 2017

(87) PCT Pub. No.: WO2016/170346
PCT Pub. Date: Oct. 27, 2016

(65) Prior Publication Data
US 2018/0110936 A1 Apr. 26, 2018

(30) Foreign Application Priority Data
Apr. 21, 2015 (GB) .................................. 1506788.7

(51) Int. Cl.
*A61M 5/32* (2006.01)
*A61M 5/20* (2006.01)
*A61M 5/31* (2006.01)

(52) U.S. Cl.
CPC ............ *A61M 5/3257* (2013.01); *A61M 5/20* (2013.01); *A61M 5/2033* (2013.01);
(Continued)

(58) Field of Classification Search
CPC .... A61M 5/20; A61M 5/2046; A61M 5/2053; A61M 5/3257; A61M 2005/2013;
(Continued)

(56) References Cited

U.S. PATENT DOCUMENTS

2006/0269484 A1* 11/2006 Knopeck ................ A61K 31/44
424/45
2009/0270804 A1 10/2009 Mesa et al.
(Continued)

FOREIGN PATENT DOCUMENTS

CA 2874165 A1 12/2013
CN 1909939 A 2/2007
(Continued)

OTHER PUBLICATIONS

International Search Report and Written Opinion dated Jul. 22, 2016, for corresponding International Application No. PCT/GB2016/051114; International Filing Date: Apr. 21, 2016 consisting of 14-pages.
(Continued)

*Primary Examiner* — Tiffany Legette
(74) *Attorney, Agent, or Firm* — Christopher & Weisberg, P.A.

(57) ABSTRACT

A medicament delivery device has a syringe, a housing, a needle shield, a biasing member and one or more blocking members. The needle shield is biased axially forwardly by the biasing member so as to selectively cover a needle of the syringe. However, the biasing member is prevented from biasing the needle shield axially forwardly until a radial movement of the blocking members has occurred, which is precipitated by a forward axial movement of the syringe. Consequently, the forward movement of the syringe releases the needle shield to automatically make safe the device.

23 Claims, 6 Drawing Sheets

(52) U.S. Cl.
CPC ........ *A61M 5/2046* (2013.01); *A61M 5/2053* (2013.01); *A61M 5/3146* (2013.01); *A61M 5/3204* (2013.01); *A61M 5/3245* (2013.01); *A61M 2005/206* (2013.01); *A61M 2005/208* (2013.01); *A61M 2005/2013* (2013.01); *A61M 2005/3247* (2013.01); *A61M 2005/3268* (2013.01)

(58) Field of Classification Search
CPC .. A61M 2005/3247; A61M 2005/3268; A61M 5/2033; A61M 5/3146; A61M 5/3204; A61M 5/3245; A61M 2005/206; A61M 2005/208
See application file for complete search history.

(56) References Cited

U.S. PATENT DOCUMENTS

| | | | | |
|---|---|---|---|---|
| 2010/0268170 | A1* | 10/2010 | Carrel | A61M 5/2033 604/198 |
| 2013/0018313 | A1* | 1/2013 | Kramer | A61M 5/2033 604/131 |
| 2013/0274662 | A1 | 10/2013 | Hourmand et al. | |
| 2013/0289490 | A1 | 10/2013 | Kemp et al. | |
| 2014/0114248 | A1 | 4/2014 | DeSalvo et al. | |

FOREIGN PATENT DOCUMENTS

| | | | |
|---|---|---|---|
| CN | 104428204 | A | 3/2015 |
| GB | 2410188 | A | 7/2005 |
| JP | 2007518507 | A | 7/2007 |
| JP | 2008508950 | A | 3/2008 |
| JP | 2013151503 | A | 8/2013 |
| JP | 2014534033 | A | 12/2014 |
| WO | 2013182859 | A | 12/2013 |
| WO | WO-2013182861 | A1 * | 12/2013 |

OTHER PUBLICATIONS

UKIPO Search Report and Written Opinion dated Oct. 13, 2015, for corresponding International Application No. GB1506788.7; International Filing Date: Apr. 21, 2015 consisting of 3-pages.

International Preliminary Report on Patentability dated Oct. 24, 2017, for corresponding International Application No. PCT/GB2016/051114, International Filing Date: Apr. 21, 2016 consisting of 8-pages.

Office Action dated Nov. 14, 2019, for corresponding Chinese Application No. 201680023304.7, consisting of 8-pages.

Japanese Office Action dated Mar. 3, 2020, for corresponding Japanese Application No. 2017-555356; consisting of 7-pages.

* cited by examiner

MEDICAMENT DELIVERY DEVICE HAVING GAS PROPELLANT

CROSS-REFERENCE TO RELATED APPLICATIONS

This application is a Submission under 35 U.S.C. § 371 for U.S. National Stage Patent Application of, and claims priority to, International Application Number PCT/GB2016/051114 entitled MEDICAMENT DELIVERY DEVICE HAVING GAS PROPELLANT, filed Apr. 21, 2016, which is related to and claims priority to Great Britain Patent Number 1506788.7, filed Apr. 21, 2015, the entirety of all of which are incorporated herein by reference.

TECHNICAL FIELD

The invention relates a medicament delivery device, particularly to a medicament delivery device having a needle shield.

BACKGROUND

Medical devices comprising automatically actuatable syringes, sometimes referred to as auto-injectors, are known. These devices include a power source, for example a compressed spring or a container of pressurised gas, which is used to deliver a dose of medicament to a patient. Such devices may include further components, such as a needle protecting shield for selectively covering a needle of the device. Further, the needle shield may be actuated during the delivery of the medicament, for example in response to the axial position of the syringe at a predetermined stage of delivery. The needle shield makes safe the device by covering the needle at certain stages of delivery and reduces the risk of potential needle stick injuries. In a final needle protecting position, the needle shield may also prevent unintentional or undesirable re-use of the device.

It is an object of certain embodiments of the invention to provide an improved medicament delivery device. Further, it is an object of embodiments of the invention to at least mitigate one or more of the problems associated with prior art arrangements.

SUMMARY OF THE INVENTION

According to the invention, there is provided a medicament delivery device comprising:
a syringe having a needle;
a housing adapted for receiving the syringe such that the syringe is axially moveable relative to the housing between a first axial syringe position and a second axial syringe position, the second axial syringe positon being axially forward of the first axial syringe position;
a needle shield axially moveable relative to the housing, the needle shield being moveable between a first axial shield position and a second axial shield position, the second axial shield positon being axially forward of the first axial shield position, for selectively covering the needle of the received syringe;
a biasing member for biasing said needle shield axially forwardly from the first axial shield position to the second axial shield position; and
at least one blocking member which is radially moveable from a first radial position to a second radial position in response to a forward axial movement of the syringe;
wherein in a first configuration the syringe is in the first axial syringe position, the needle shield is in the first axial shield position and the blocking member is in the first radial position, such that the needle is covered by the needle shield and the blocking member prevents the biasing member from biasing the needle shield to the second axial shield position;
in a second configuration the syringe is in the second axial syringe position, the needle shield is in the first axial shield position, or a position axially rearward of the first axial shield position, and the blocking member is in the second radial position, by virtue of forward axial movement of the syringe, such that the blocking member permits the biasing member to bias the needle shield to the second axial shield position; and
in a third configuration the syringe is in the second axial syringe position, or a position axially forward of the second axial syringe position, and the needle shield is in the second axial shield position, such that the needle is covered by the needle shield;
wherein the second configuration is subsequent to the first configuration and the third configuration is subsequent to the second configuration. This arrangement may enable fast and effective delivery of a medicament to a patient in a manner which reduces the risk of undesirable needle-stick injuries. Further, the needle may be hidden from view prior to, during and after delivery, which may reduce anxiety associated with the use of medicament delivery devices, especially devices which may be used to administer a medicament to children.

The device may exhibit a further configuration in which the needle shield is in a positon axially rearward of the first axial shield position. Moreover, the further configuration may be subsequent to the first configuration and prior to the second configuration. This arrangement may permit the needle shield to move axially rearwardly upon placement of the device upon an injection site.

A rearward axial movement of the needle shield may compress the biasing member so as to provide at least in part the biasing force for biasing the needle shield. Additionally, or alternatively, the forward axial movement of the syringe may compress the biasing member so as to provide at least in part the biasing force for biasing the needle shield. Either of these two arrangements have the advantage that the biasing means may not be stored fully compressed, thereby reducing the risk of creep affecting the performance of the biasing member in use.

In certain embodiments, in the first configuration the housing may prevent rearward axial movement of the needle shield. In certain embodiments, in the third configuration the at least one blocking member may prevent rearward axial movement of the needle shield. Preventing axial rearward movement of the needle shield in the third configuration may prevent re-exposure of the needle unintended or undesirable re-use of the device.

Optionally, the needle shield may comprise the at least one blocking member. Further, the at least one blocking member may comprise an arm. In certain embodiments, the arm may extend axially rearwardly at the rear the needle shield. In certain embodiments, the at least one blocking member may comprise a radial protrusion. Optionally, the radial protrusion extends radially inwardly. Further, the radial protrusion may provide a forward facing abutment surface for abutment with the housing. Additionally or alternatively, the at least one blocking member may comprise one or more apertures extending at least partially through a portion of the needle shield. In certain embodiments, the one or more apertures may provide a or a further forward facing abutment surface for abutment with the housing.

In certain embodiments, the at least one blocking member may be selectively engageable with an engaging means of the housing to prevent forward axial movement of the needle shield.

In certain embodiments, the at least one blocking member may be radially flexible. Further, the biasing member may comprise a compression spring.

Optionally, the device may further comprise a power source actuatable to move the syringe axially forward. In certain embodiments, the power source may comprise a volume of a liquefied gas propellant. The power source may comprise a propellant which includes a hydrofluoroalkane ("HFA"). The power source may comprise a propellant which includes a hydrofluoroolefin ("HFO"). In certain embodiments, the power source may comprise a compression spring.

The device may further comprise an actuating means for actuating the device. The actuating means may comprise an outer casing which is axially moveable to actuate the device. Further, the device may also comprise a priming means for priming the device. The priming means may comprise an end cap which is removable to prime to device.

BRIEF DESCRIPTION OF THE DRAWINGS

Embodiments of the invention will now be described by way of example only, with reference to the accompanying figures, in which.

DETAILED DESCRIPTION

Figure 1:
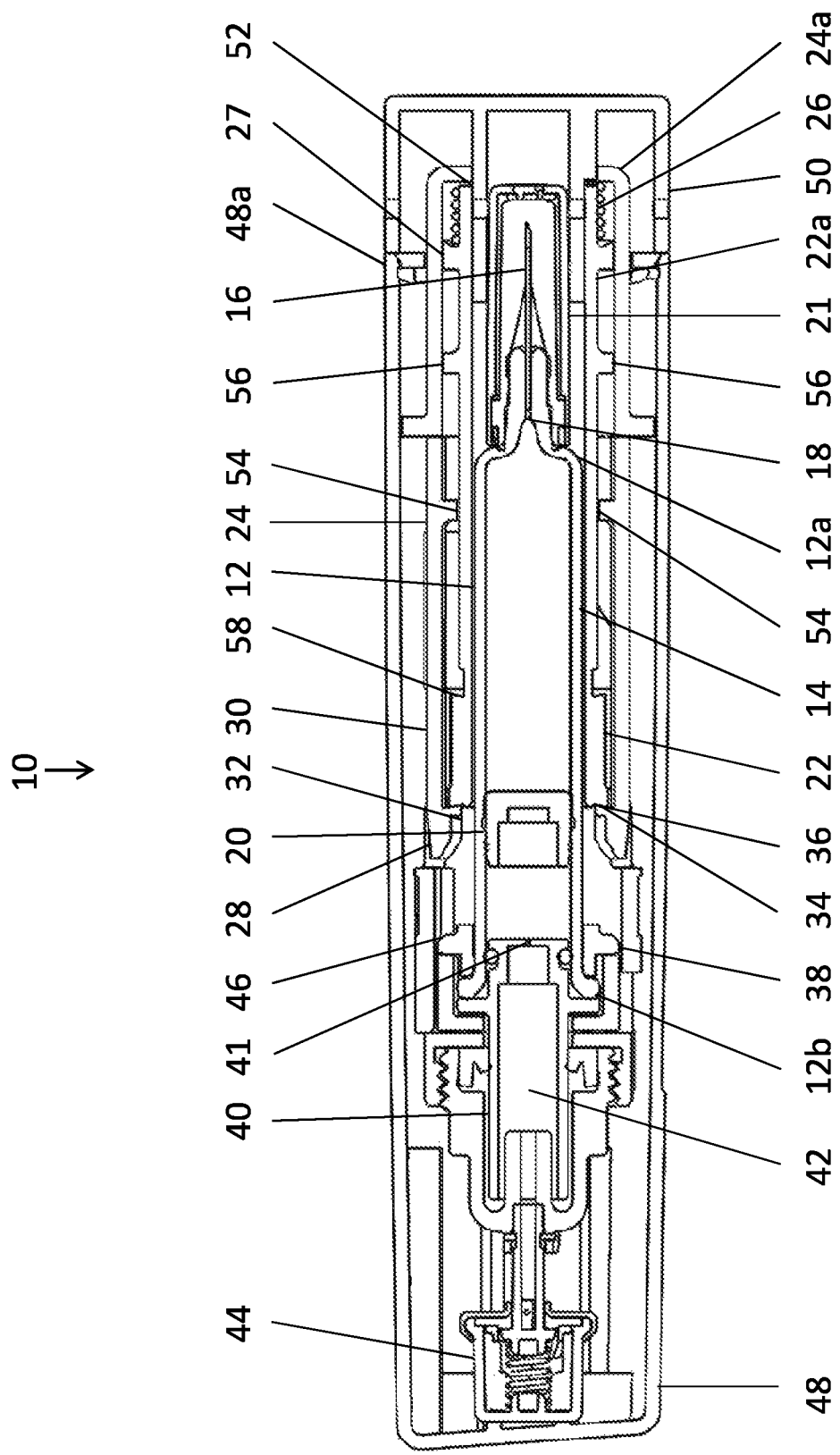
FIG. 1 is a cross-sectional view of a medicament delivery device according to an embodiment of the invention.

FIGS. 1 to 6 illustrate a device 10 according to an embodiment of the invention. The device 10 is an autoinjector for delivering a dose of medicament to a patient. The device 10 includes a syringe 12 having a barrel 14 and a needle 16. The barrel 14 has an open end 18 to which the needle 16 is attached. Further, the barrel 14 contains a stopper 20 which is axially slideable within the barrel 14. As illustrated in FIG. 1, the syringe 12 may also include a removable needle sheath 21.

The device 10 further includes a syringe housing 22. The housing 22 is adapted for receiving the syringe 12 such that the syringe 12 is axially movable relative to the housing 22. In certain embodiments, the housing 22 may comprise a sleeve-like member. In the illustrated embodiment, the syringe 12 is at least partially received within the housing 22 and is axially slideable therein. The syringe 12 is axially moveable relative to the housing 22 between a first axial syringe position and a second axial syringe position. The second axial syringe position is axially forward of the first axial syringe position.

The device 10 also includes a protective needle shield 24. The needle shield is associated with a front end 12b of the syringe 12 and is axially movable relative to the housing 22. In certain embodiments, the needle shield 24 may comprise a sleeve-like member. Further, the needle shield 24 may be slideably engaged with the housing 22. In the illustrated embodiment, the needle shield 24 is slideably engaged with the housing 22 such that the housing 22 is at least partially received within the needle shield 24. The needle shield 24 is moveable relative to the housing 22 between a first axial shield position and a second axial shield position. The second axial shield position is axially forward of the first axial shield position. Throughout the specification, references to the forward axial direction are intended to mean towards the front end of the device 10, the front end being that at which the needle shield 24 is provided. Conversely, references to the rearward axial direction are intended to mean away from the front end.

The device 10 also includes a biasing member 26 and one or more blocking members 28. The biasing member 26 biases the needle shield 24 axially forwardly towards the second axial shield position. In certain embodiments, the biasing member 26 may be provided as a compression spring 26. The spring 26 may be held in at least a partially compressed state, i.e. having stored potential energy, between a front end 24a of the needle shield 24 and a support member 27 provided adjacent a front end 22a of the housing 22. The spring 26 may be held in at least a partially compressed state when the needle shield 24 is in the first axial shield position.

The one or more blocking members 28 may be associated with the needle shield 24. In the illustrated embodiment, the blocking members 28 are formed as part of the needle shield 24. As is also illustrated, the blocking members 28 may be provided about a circumference of the needle shield 24. Of course, it will be understood that in alternative embodiments the one or more blocking members 28 may be separate from the needle shield 24. In certain embodiments, the one or more blocking members may be suitably attached to the needle shield 24. The blocking members 28 are radially moveable between a first radial position and a second radial position in response to a forward axial movement of the syringe 12.

Each of the one or more blocking members 28 may comprise an arm 30. Additionally, or alternatively, each of the one or more blocking members 28 may comprise a radial protrusion 32. In certain embodiments, the one or more blocking members 28 may comprise one or more apertures extending at least partially through a portion of the needle shield 24. The arms 30 may extend axially rearwardly at the rear of the needle shield 24. The arms 30 may be radially flexible, i.e. elastically deformable, so as to permit movement of the blocking members 28 between the first and second radial positions. The radial protrusions 32 may project radially inwardly, i.e. toward a centreline of the device 10. This arrangement is shown in the illustrated embodiment. However, in certain embodiments the protrusions 32 may instead project radially outwardly. As is also shown in the illustrated embodiment, each of the radial protrusions 32 may provide a forward facing abutment surface 34. In certain embodiments, the one or more apertures extending at least partially through a portion of the needle shield 24 may provide the forward facing abutment surface 34.

The housing 22 includes one or more an engaging features 36. The engaging features 36 may be configured for engagement with the abutment surfaces 34 of the blocking members 28. As such, the engaging features 36 may be provided about a circumference of the housing 22. The abutment surfaces 34 may be engageable with the engaging features 36 when the blocking members 28 are in the first radial position. Consequently, engagement of the abutment surfaces 34 and the engaging features 36 may prevent forward axial movement of the needle shield 24 relative to the housing 22. This interaction is described in more detail below.

The device 10 may further include a syringe support 38, a piston 40 and/or a power source 44. The syringe support 38 may retain the syringe 12 within the device 10. In the illustrated embodiment, the syringe support 38 is associated with a rear end 12b of the syringe 12. However, in alternative embodiments, the syringe support 38 may be associated with the syringe 12 at any point along the length of the syringe 12. The syringe support 38 may serve as a shield release mechanism 38 for moving the blocking members 28 to the second radial position. The release mechanism 38 may move axially forwardly together with the syringe 12 relative to the housing 22. Further, the release mechanism 38 may include one or more forward facing surfaces 46 adapted to contact the blocking members 28 during axial forward movement of the syringe 12.

The shield release mechanism 38, as described with reference to the illustrated embodiment, is not limiting to the present invention. The shield release mechanism 38 may be provided by any suitable alterative means, for example, the release mechanism 38 may be provided on the piston 40.

In the illustrated embodiment, the one or more surfaces 46 extend around a circumference of the release mechanism 38. Of course, in other embodiments, the one or more surfaces 46 may extend over only a portion of the release mechanism 38. The one or more surfaces 46 may be chamfered, angled or profiled such that once the one or more surfaces 46 has contacted the one or more blocking members 38 further axial forward movement of the release mechanism 38 will radially displace the blocking members 28 out of axial alignment with the abutment surfaces 34, so as to permit axial forward movement of the needle shield 24 with respect to the housing 22. In the illustrated embodiment, the blocking members 28 are displaced radially outwardly in response to axial forward movement of the syringe 12 and the release mechanism 38.

As illustrated in the accompanying figures, the one or more blocking members 28 may each be chamfered, angled or profiled to facilitate their radial movement when contacted by the release mechanism 38.

The piston 40 and power source 44 may cooperate together to move the syringe 12 axially forwardly relative to the housing 22. The piston 40 partially defines a volume 42 which may vary in size due to the axial position of the piston 40. Consequently, the piston 40 is axially moveable in response to pressurisation, i.e. an increase in pressure, of the volume 42. Further, the volume 42 may be in fluid communication with the barrel 14 of the syringe 12. As can be seen in the accompanying figures, the piston 40 includes an aperture 41 permitting fluid communication between the volume 42 and the barrel 14. The stopper 20 is axially moveable within the barrel 14 in response to pressurisation of the barrel 14 axially rearward of the stopper 20.

The power source 44 may comprise a propellant source 44 for supplying a propellant for providing a vapour pressure. The propellant source 44 may supply a propellant for providing a vapour pressure within the volume 42 sufficient to cause axial movement of the piston 40 from the first axial piston positon to the second axial piston position. Further, the propellant source 44 may supply a propellant for providing a vapour pressure sufficient to cause axial movement of the stopper 20 within the barrel 14 and, thus, deliver a dose of the medicament. The pressure sufficient to cause axial movement of the piston 40 may be less than the pressure sufficient to cause axial movement of the stopper 20. Therefore, the stopper 20 may not be axially movable with in the barrel 14 until pressurisation of the volume 42 defined by the piston 40 and the insertion chamber 42 has moved the syringe 12 to the second axial syringe positon.

The propellant may be any suitable propellant for providing a vapour pressure to the volume 42. In certain embodiments, the propellant may be a liquefied gas that vaporises to provide a vapour pressure. In certain embodiments, the propellant may be or contain a hydrofluoroalkane ("HFA"), for example HFA 341a, HFA227, HFA 422D, HFA 507, or HFA 410A. In certain embodiments, the propellant may be or contain a hydrofluoroolefin ("HFO"), such as HFO 1234yf or HFO 1234ze.

The described and illustrated means of moving the syringe 12 axially forwardly is not limiting to the present invention. It will be understood that any suitable alternative means may be incorporated within the device 10 for the moving the syringe axially forwardly, for example a compression spring or a plunger rod.

The device 10 further includes an actuating means 48 and a priming means 50. The actuating means 48 may be provided as an outer casing 48. In the illustrated embodiment, the outer casing 48 is adapted for receiving the syringe housing 22 such that the housing 22 is axially movable relative to the casing 48. As illustrated in the accompanying figures, the housing 22 is at least partially received within the outer casing 48 and is axially slideable therein. Rearward axial movement of the housing 24 relative to the casing 48 actuates the device 10, thus delivering a dose of medicament to a patient. Rearward axial movement of the housing 24 relative to the outer casing 48 may compress the propellant source 44 so as to initiate release of the propellant and pressurise the volume 42. Rearward axial movement of the housing 22 relative to the casing 48 may occur when a user actuates the device 10 by holding the outer casing 48 and pressing the front end of the needle shield 24 against the injection site. From the perspective of the user, the rearward movement of housing 22 is seen as a forward movement of the outer casing 48.

The priming means 50 may be provided as an end cap 50 attachable to a front end 48a of the casing 48. In other embodiments, priming means may be alternatively provided, for example as a pin removable from the device 10 in order to prime the device. With reference to the invention, priming of the device 10 is readying the device 10 in some manner to deliver a dose of medicament, i.e. the primed device 10 is no longer in a pre-use state, where "pre-use state" refers to the state of the device 10 during shipping and storage prior to use. The end cap 50 may be adapted to engage with the front end 48a of the casing 48, for example by frictional engagement or snap-fit engagement. Further, the end cap 16 may be adapted to engage with the removable needle sheath 21. The device 10 cannot be actuated when the end cap 50 is attached to the front end 48a of the casing 48. Further, the casing 48 and the end cap 50 may completely encapsulate the syringe 12, the housing 22 and the needle shield 24 when the end cap 50 is attached to the front end 48a of the casing 48 the device 10. The device 10 may be primed, i.e. ready to deliver a dose of the medicament, when the end cap 50 is removed from the front end 48a of the casing 48. Once primed, the device 10 may be actuated, i.e. the housing 22 moved axially rearwardly within the casing 48.

FIGS. 1 to 6 illustrate the device 10 at various stages of delivery of the medicament. During delivery the medicament is expelled from the device 10 into an injection site of the patient. The various stages of delivery may be characterised by configurations of the device 10 which define the respective axial positions of the syringe 12, the housing 22 and the needle shield 24. Certain embodiments may exhibit a first configuration, a second configuration and a third configuration. In such embodiments, device is operable such that the second configuration is subsequent to the first configuration and the third configuration is subsequent to the second configuration. Certain embodiments may also exhibit a further configuration. In such embodiments, the further configuration may be subsequent to the first configuration and prior to the second configuration The different configurations will now be described with reference to the various stages of delivery illustrated in the accompanying figures.

FIG. 1 illustrates the device 10 in a pre-use state. The syringe 12 is pre-filled with the medicament. The front end cap 50 is attached to the device 10 and, as such, the device 10 cannot be actuated. The needle 16 in not visible to the user or the patient when the end cap 50 is attached to the front end 48a of the casing 48. FIG. 1 illustrates the device 10 in the first configuration. In the first configuration the syringe 12 is in the first axial syringe position, the needle shield 24 is in the first axial shield position and the blocking members 28 are in the first radial position. In the first configuration the needle 16 is covered by the needle shield 24 and the blocking members 28 prevent the biasing member 26 from biasing the needle shield 24 to the second axial shield position In the first radial position of the blocking members 28, the abutment surfaces 34 are engaged with the engaging features 36 of the housing 22. It is this arrangement which prevents the forward axial movement of the needle shield 24 relative to the housing 22, as the engaging features 36 interrupt a forward axial path of the blocking members 26.

In the first radial position the arms 30 may be in a substantially unflexed state, i.e. little or no bending stresses are present in the arms 30.

Rearward axial movement of the needle shield 24 may be possible when the device 10 is in the first configuration. In the illustrated embodiment, rearward axial movement of the needle shield 24 is possible by virtue of a gap 52 provided between the front end 22a of the housing 22 and the front end 24a of the needle shield 24. The needle shield 24 may by moved axially rearwardly relative to the housing 22 until the front end 22a of the housing 22 contacts the front end 24a of the needle shield 24. However, rearward movement of the needle shield 24 is may not be possible with the end cap 50 attached to the casing 48.

In the first configuration the biasing member 26 may not be fully compressed. Rearward axial movement of the needle shield 24 relative to the housing 22 may compress the biasing member 26 so as to provide at least in part the biasing force for biasing the needle shield 24. However, in the first configuration the biasing member 26 may be partially compressed. The biasing member 26 may bias the needle shield 24 axially forwardly, so as to maintain the gap 52.

Figure 2:
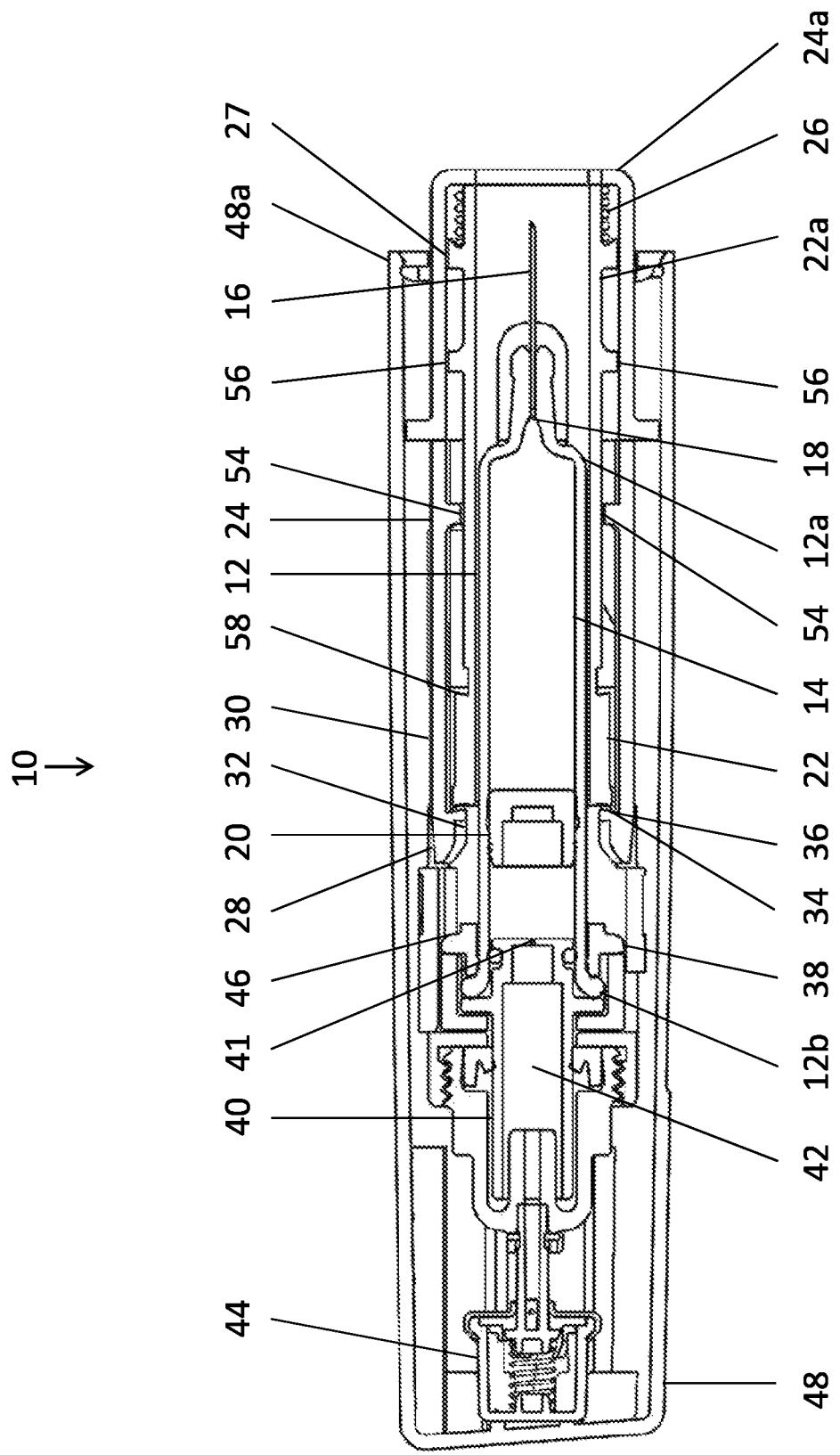
FIG. 2 is a cross-sectional view of the device of FIG. 1 as it would appear partially pressed against an injection site after priming of the device.

FIG. 2 illustrates the device 10 as it would appear ready for use and with the front end 24a of the needle shield 24 pressed partially against the injection site. The front end cap 50 is removed from the front end 48a of the casing 48 and, as such, the device 10 can be actuated to cause delivery of the medicament. Removal of the front end cap 50 may remove the removable needle sheath 21. FIG. 2 illustrates the device 10 in the further configuration. In the further configuration the needle shield is in a positon axially rearward of the first axial shield position.

FIG. 2 illustrates the biasing member 26 fully compressed. Taking the device 10 and partially pressing the front end 24a of the needle shield 24 against the injection site causes the needle shield 24 to move axially rearwardly with respect to the housing 22. This action closes the gap 52 between the front end 22a of the housing 22 and the front end 24a of the needle shield 24. Consequently, the needle shield 24 may no longer be moved axially rearwardly relative to the housing 22. However, the housing 22 has not moved axially rearwardly within the casing 48, at least not sufficiently, so as to actuate the device 10.

In the illustrated embodiment, reward axial movement of the needle shield 24 results in the abutment surfaces 34 disengaging with the engaging features 36 (as the blocking members 28 move axially rearwardly together with the needle shield 24). However, the blocking members 28 remain in the first radial position. Consequently, if the device 10 were removed from the injection site, prior to actuation of the device 10, the biasing member 26 may bias the needle shield 24 axially forwardly until the abutment surfaces 34 reengage with the engaging features 36. In other words, the engaging features 36 still interrupt the forward axial path of the blocking members 26.

In certain embodiments, the device 10 may not exhibit the further configuration. In such embodiments, there may be no gap 52 provided between the front end 22a of the housing 22 and the front end 24a of the needle shield 24. Consequently, the needle shield 24 may not be moved axially rearwardly from the first axial shield position relative to the housing 22.

Figure 3:
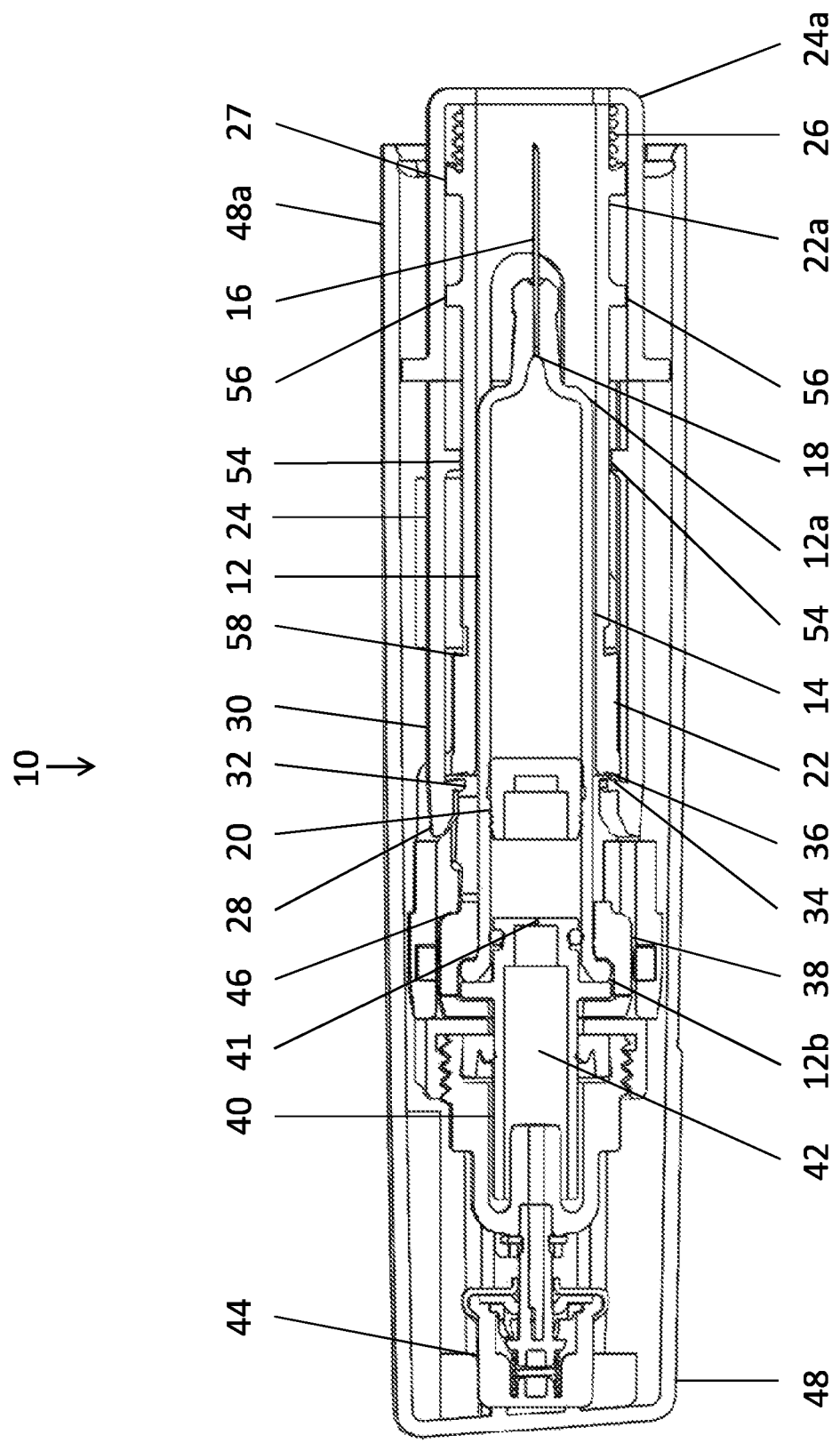
FIG. 3 is a cross-sectional view of the device of FIG. 1 as it would appear pressed against an injection site prior to delivery of a medicament.

FIG. 3 illustrates the device 10 as it would appear with the needle shield 24 pressed fully against the injection site at the moment the device 10 is actuated. FIG. 3 illustrates the device 10 in the further configuration, as the respective axial positions of the syringe 12 and the needle shield 24 relative to the housing 22 remain unchanged from the arrangement illustrated in FIG. 2. Pressing the device 10 fully against the injection site causes the syringe 12, the housing 22 and the needle shield 24 to move axially rearwardly together relative to the outer casing 48. In the illustrated embodiment, this rearward axial movement actuates the device 10, i.e. releases the propellant contained within the power source 44.

Figure 4:
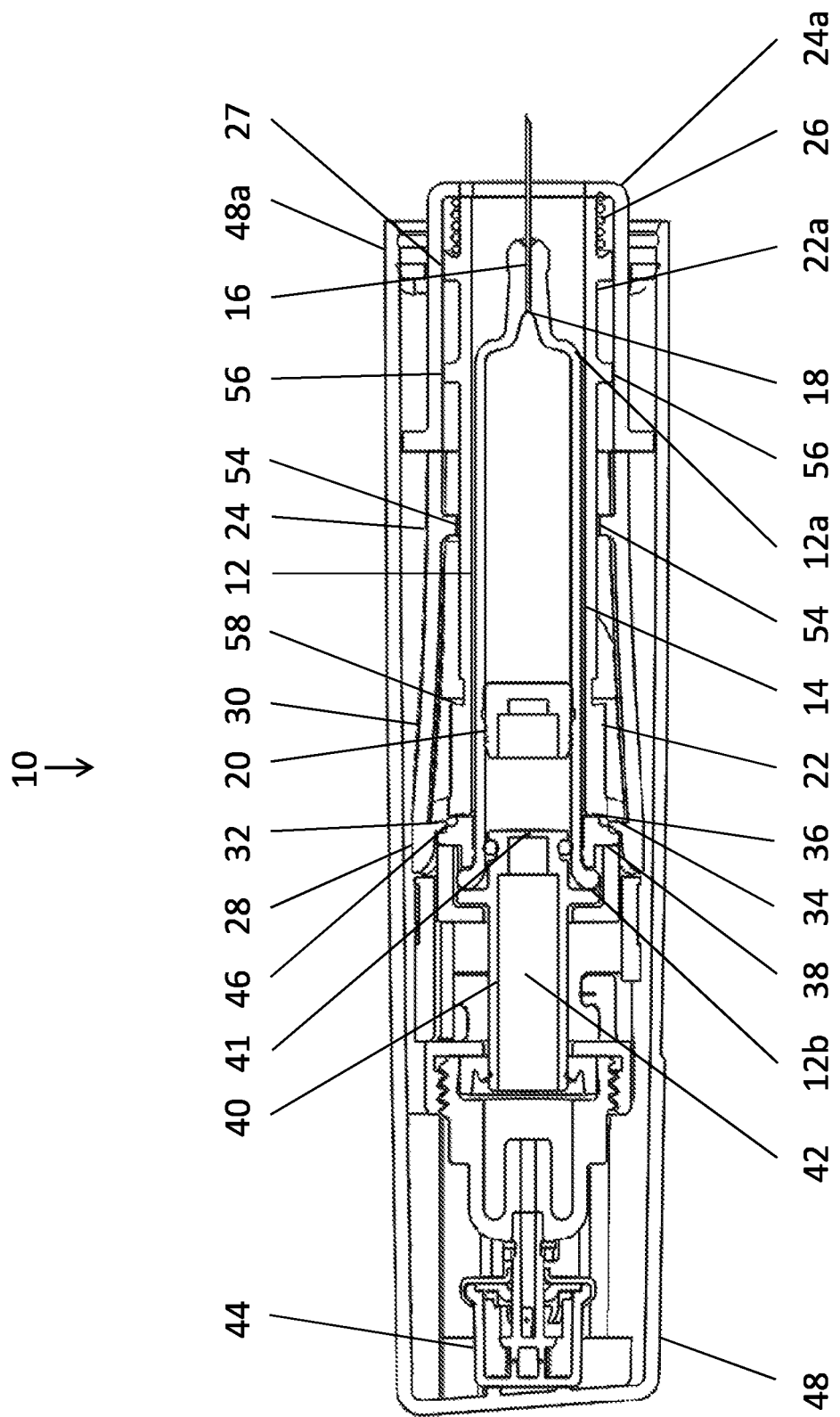
FIG. 4 is a cross-sectional view of the device of FIG. 1 as it would appear pressed against an injection site during delivery of the medicament.

FIG. 4 illustrates the device 10 as it would appear with the needle shield 24 pressed fully against the injection site. The device 10 has been actuated and, as such, the needle 16 may now protrude from the front end 24a of the needle shield 24. FIG. 4 illustrates the device 10 in the second configuration. In the second configuration the syringe 12 is in the second axial syringe position, the needle shield 24 is in the first axial shield position, or a positon axially rearward of the first axial shield position, and the blocking members 28 are in the second radial position. In the second configuration the blocking members 28 permit the biasing member 26 to bias the needle shield 24 to the second axial shield position. In the second configuration, the positon of the needle shield 24 may be in a positon axially rearward of the first axial shield position, such that the position of the needle shield 24 corresponds to the position of the needle shield 24 in the further configuration. In alterative embodiments, the positon of the needle shield 24 may correspond to the first axial shield position, for example in embodiments without the gap 52.

Upon actuation of the device 10, release of the propellant contained within the power source 44 may pressurise the volume 42. Consequently, the piston 40 moves axially forwardly and drives the syringe support 38 and the syringe 12 axially forwardly relative to the housing 22. If the front end 24*a* of the needle shield 24 is pressed against the injection site, forward axial movement of the syringe 12 inserts the needle 16 into the patient.

As the syringe 12 moves axially forwardly to the second axial syringe positon, the release mechanism 38 displaces the one or more blocking members 28 to the second radial position. The forward facing surfaces 46 of the release mechanism 38 contact the respective blocking members 28 and urge the blocking members 28 radially outward. In the second radial position the arms 30 may be in a flexed state, i.e. elastically deformed, such that bending stresses resulting from the flexing of the arms 30 bias the arms toward the first radial position. The release mechanism 38 moves the blocking members 28 such that the engaging features 36 do not interrupt the forward axial path of the blocking members 28. The biasing member 26 is now free to bias the needle shield 24 to the second axial shield position. In use, the needle shield 24 may be prevented from moving axially forwardly by virtue of contact of the front end 24*a* of the needle shield 24 with the injection site.

In certain embodiments, the forward axial movement of the syringe may compress the biasing member so as to provide at least in part the biasing force for biasing the needle shield.

Figure 5:
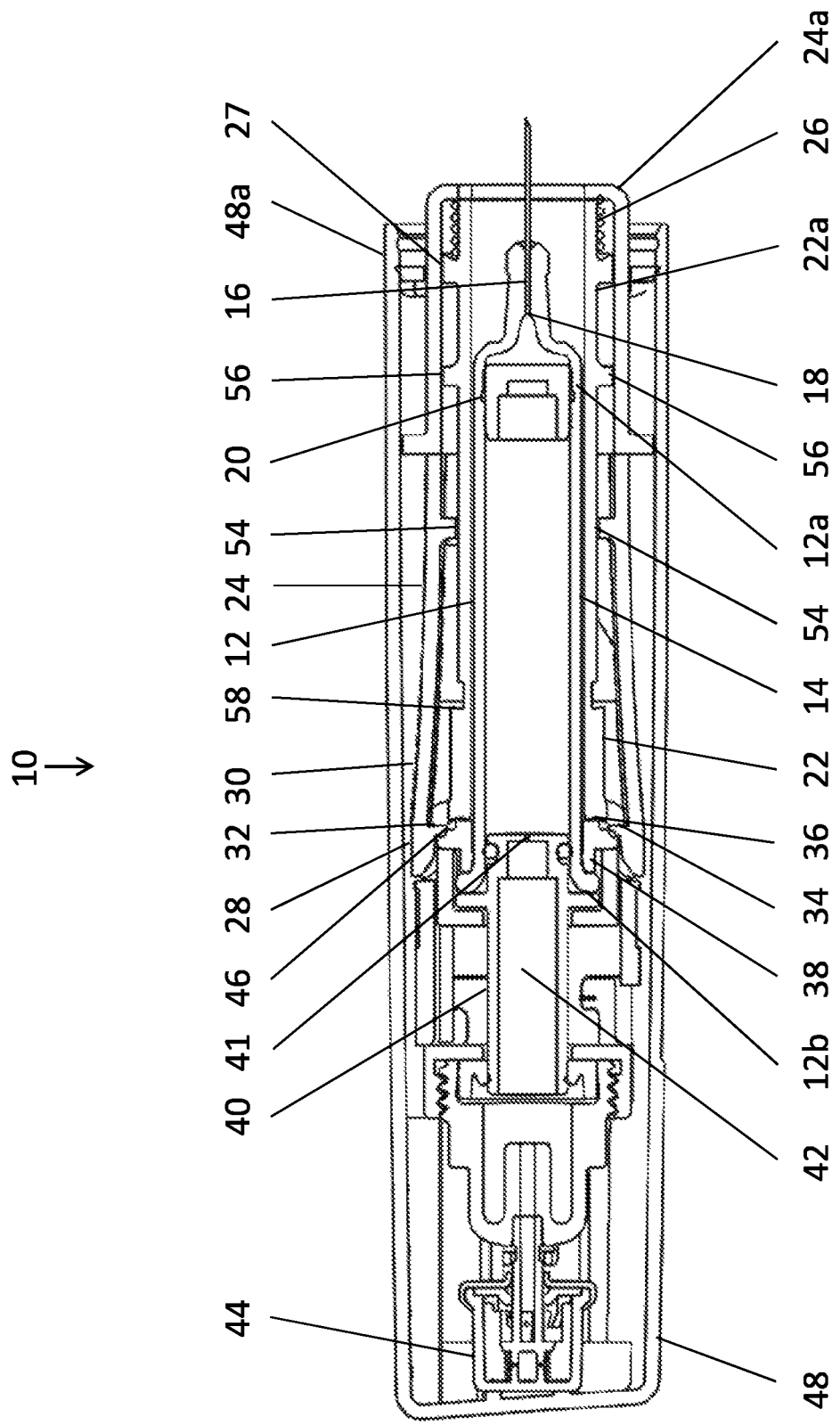
FIG. 5 is a cross-sectional view of the device of FIG. 1 as it would appear pressed against an injection site after delivery of the medicament.

FIG. 5 illustrates the device 10 as it would appear with the needle shield 24 pressed fully against the injection site after delivery of the medicament to the patient. FIG. 5 illustrates the device 10 in the second configuration, as the respective axial positions of the syringe 12 and the needle shield 24 relative to the housing 22 remain unchanged from the arrangement illustrated in FIG. 4. Continued release of the propellant may result in axial forward movement of the stopper 20 within the barrel 14 and delivery a dose of the medicament to the patient.

Figure 6:
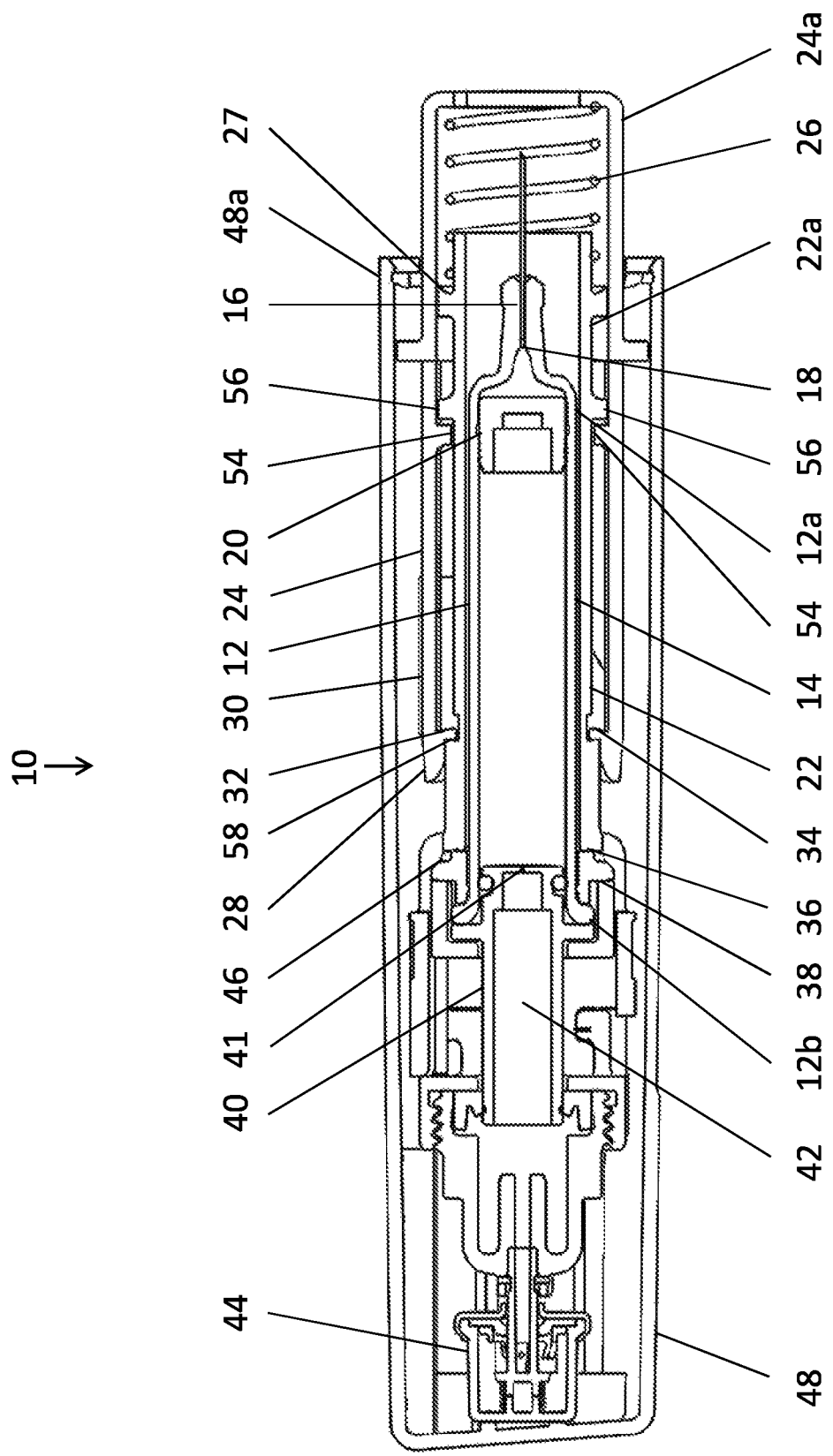
FIG. 6 is a cross-sectional view of the device of FIG. 1 after removal of the device from the injection site.

FIG. 6 illustrates the device 10 in a used state, i.e. the device 10 has been removed from the injection site and the needle 16 is protected by the advanced needle shield 24.

FIG. 6 illustrates the device 10 in the third configuration. In the third configuration the syringe 12 is in the second axial syringe position, or a position axially forward of the second axial syringe position, and the needle shield is in the second axial shield position. In the third configuration the needle 16 is covered by the needle shield 24. Removal of the device 10 from the injection site may permit forward axial movement of the needle shield 24, as movement of the needle shield 24 may no longer be limited by contact of the front end 24*a* of the needle shield 24 with the injection site.

In the third configuration the syringe 12 may be in a position axially forward of the second axial syringe position. The syringe 12 may move axially forward of the second syringe position in response to the device 10 being removed from the injection site, as contact of the front end 12*a* of the syringe 12 with the injection site during delivery of the medicament may have limited the axial forward movement of the syringe 12.

Axial forward movement of the needle shield 24 relative to the housing 22 may be limited by one or more corresponding stops 54, 56 provided on the housing 22 and the needle shield 24, respectively. It will be understood that, in alternative embodiments, the forward axial movement of the needle shield 24 relative to the housing 22 may be limited by any suitable means. In the used state, the needle shield 24 may be locked to prevent axially rearward movement of the needle shield 24 relative to the housing 22. In the illustrated embodiment, the arms 30 have moved radially inward, biased by the bending stresses resulting from the flexing of the arms 30. Consequently, the blocking members 28 have engaged with retaining components 58 provided on the housing 22. The retaining components 58 interrupt the rearward axial path of the blocking members 26, thus preventing the needle shield 24 from moving axially rearward.

In the third configuration, the device 10 may be in a safe state. In certain embodiments, the device 10 is not intended for re-use and the device 10 is disposed of after actuation. However, in alternative embodiments, the device 10 may be re-set by displacing the blocking members 28 radially outward and moving the syringe 12, the housing 22 and needle shield 24 to their respective initial axial positions. This may be desirable, for example, were the device 10 is used as a training aid.

The aforementioned configurations define the respective axial positions of the syringe 12 and the needle shield 24 relative to the housing 22. The configurations do not necessarily define the respective axial positions of the syringe 12, the needle shield 24 or the housing 22 relative to the outer case 48. Certain embodiments may not have an outer case 48. Further, while the configurations define the radial positions of the one or more blocking members 28 by reference to the first and second radial positon. The present invention is not limited to embodiments in which the first radial position is radially inward of the second radial positon.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A medicament delivery device comprising:
   a syringe having a needle;
   a housing adapted for receiving the syringe such that the syringe is axially moveable relative to the housing between a first axial syringe position and a second axial syringe position, the second axial syringe position being axially forward of the first axial syringe position;
   a needle shield axially moveable relative to the housing, the needle shield being moveable between a first axial shield position and a second axial shield position, the second axial shield position being axially forward of the first axial shield position, for selectively covering the needle of the syringe;

a biasing member for biasing said needle shield axially forwardly from the first axial shield position to the second axial shield position; and at least one blocking member which is radially moveable from a first radial position to a second radial position in response to a forward axial movement of the syringe;

in a first configuration the syringe is in the first axial syringe position, the needle shield is in the first axial shield position and the at least one blocking member is in the first radial position, such that the needle is covered by the needle shield and the at least one blocking member prevents the biasing member from biasing the needle shield to the second axial shield position;

in a second configuration the syringe is in the second axial syringe position, the needle shield is in the first axial shield position, or a position axially rearward of the first axial shield position, and the at least one blocking member is in the second radial position, by virtue of forward axial movement of the syringe, such that the at least one blocking member permits the biasing member to bias the needle shield to the second axial shield position; and in a third configuration the syringe is in the second axial syringe position, or a position axially forward of the second axial syringe position, and the needle shield is in the second axial shield position, such that the needle is covered by the needle shield;

the second configuration is subsequent to the first configuration and the third configuration is subsequent to the second configuration; and where the at least one blocking member is formed as a part of the needle shield.

2. The medicament delivery device of claim 1, wherein the forward axial movement of the syringe compresses the biasing member so as to provide at least in part a biasing force for biasing the needle shield.

3. The medicament delivery device of claim 1, wherein in the first configuration the housing prevents rearward axial movement of the needle shield.

4. The medicament delivery device of claim 1, wherein in the third configuration the at least one blocking member prevents rearward axial movement of the needle shield.

5. The medicament delivery device of claim 1, wherein an abutment surface of the at least one blocking member is configured to be selectively engageable with an engaging means of the housing so as to prevent forward axial movement of the needle shield.

6. The medicament delivery device of claim 1, wherein the at least one blocking member is radially flexible.

7. The medicament delivery device of claim 1, wherein the biasing member comprises a compression spring.

8. The medicament delivery device of claim 1, wherein in a further configuration
the needle shield is in a position axially rearward of the first axial shield position; and
the further configuration is subsequent to the first configuration and prior to the second configuration.

9. The medicament delivery device of claim 8, wherein a rearward axial movement of the needle shield compresses the biasing member so as to provide at least in part a biasing force for biasing the needle shield.

10. The medicament delivery device of claim 1, wherein the at least one blocking member comprises an arm.

11. The medicament delivery device of claim 10, wherein the arm extends axially rearwardly at a rear of the needle shield.

12. The medicament delivery device of claim 1, further comprising an actuating means for actuating the medicament delivery device.

13. The medicament delivery device of claim 12, wherein the actuating means comprises an outer casing which is axially moveable to actuate the medicament delivery device.

14. The medicament delivery device of claim 1, further comprising a priming means for priming the medicament deliver device.

15. The medicament delivery device of claim 14, wherein the priming means comprises an end cap which is removable to prime the medicament delivery device.

16. The medicament delivery device of claim 1, wherein the at least one blocking member comprises a radial protrusion.

17. The medicament delivery device of claim 16, wherein the radial protrusion extends radially inwardly.

18. The medicament delivery device of claim 16, wherein the radial protrusion provides a forward facing abutment surface for abutment with the housing.

19. The medicament delivery device of claim 1, further comprising a power source actuatable to move the syringe axially forward.

20. The medicament delivery device of claim 19, wherein the power source comprises a volume of a liquefied gas propellant.

21. The medicament delivery device of claim 19, wherein the power source comprises a propellant which includes a hydrofluoroalkane ("HFA").

22. The medicament delivery device of claim 19, wherein the power source comprises a propellant which includes a hydrofluoroolefin ("HFO").

23. The medicament delivery device claim 19, wherein the power source comprises a compression spring.

* * * * *